United States Patent [19]

Markstein et al.

[11] Patent Number: 4,855,306

[45] Date of Patent: Aug. 8, 1989

[54] USES OF DOPAMINE RECEPTOR AGONISTS

[75] Inventors: Rudolf Markstein, Rheinfelden, Fed. Rep. of Germany; Jose Palacios, Basel, Switzerland

[73] Assignee: Sandoz Ltd., Basel, Switzerland

[21] Appl. No.: 178,668

[22] Filed: Apr. 7, 1988

[30] Foreign Application Priority Data

| Apr. 10, 1987 | [GB] | United Kingdom | 8708626 |
| Apr. 14, 1987 | [GB] | United Kingdom | 8708898 |
| Apr. 28, 1987 | [GB] | United Kingdom | 8710062 |
| Aug. 28, 1987 | [GB] | United Kingdom | 8720366 |

[51] Int. Cl.$^4$ ............................... A61K 31/00
[52] U.S. Cl. .................................................. 514/280
[58] Field of Search .................................... 514/280

[56] References Cited

PUBLICATIONS

Chem. Abst. 104 (1986)-225087z.

*Primary Examiner*—Stanley J. Friedman
*Attorney, Agent, or Firm*—Gerald D. Sharkin; Robert S. Honor; Thomas O. McGovern

[57] ABSTRACT

Selective dopamine D1 receptor agonists for use in the treatment of primary degenerative dementia, depression, anxiety, obesity or schizophrenia.

7 Claims, No Drawings

USES OF DOPAMINE RECEPTOR AGONISTS

The present invention relates to new uses of dopamine receptor agonists.

More particularly the present invention relates to the use of selective dopamine D1 receptor agonists for the treatment of primary degenerative dementia, e.g. senile dementia, particularly of the Alzheimer type.

Selective dopamine D1 receptor agonists are drugs producing therapeutic actions which are predominantly mediated by dopamine receptors of the D1 type (D1 receptors). D1 receptors are defined on the widely accepted classification originally based on biochemical criteria, disclosed by Kebabian and Calne in Nature, 277: 93–96 (1979).

Senile dementia, particularly senile dementia of the Alzheimer type (SDAT), is one of the most common causes of metal deterioration in the elderly. This brain disease produces a progressive deterioration of cognitive functions, affect and behaviour, leading to the clinical syndrome of dementia.

SDATT is characterized neuropathologically by the presence of widespread senile plaques and neurofibrillary tangles in the cerebral cortex and in limbic structures, particularly the hippocampal formation. Neurochamically, a marked loss of presynaptic cholinergic markers in the cortex and hippocampus has been observed in SDAT brains. Besides the cholinergic deficit, many other neurochemical changes have been reported in the brains of SDAT patients. However dopamine receptors have not been extensively studied in SDAT.

In accordance with the present invention it has now surprisingly been found that in SDAT patients D1 receiptor densities were markedly and selectively decreased in the hippocampus.

As compared to controls, the decrease of D1 binding in the SDAT hippocampus represented the 89 % in the dentate gyrus (2P<0.022), the 74 % in the CA3 (2P<0.007), and the 57 % in the CA1 (2P <0.007).

The decrease of D1 receptor densities has been found using quantitative autoradiography and newly developed selective ligands for D1 and D2 receptors and examining in detail the distribution of D1 and D2 receptors in the control human brain and the alterations in the density and localization of these receptors in SDAT patients. The dopaine antagonist [$^3$H]SCH 23390 [Iorio et al., J. Pharmacol. Exp. Ther., 226 (1983), 462–468]has been used as a ligand.

Brains were obtained at autopsy from 15 subjects with no known hitory of neurologic or psychiatric disease (8 male and 7 female; mean age 65±3 years; mean postmortem delay 10.7±h) and 7 patients witha diagnosis of SDAT (2 male and 5 female; mean age 84±2 years; postmortem delay 12.9 ±2 h) were included in this study. SDAT was confirmed histopathologically by the presence of senile plaques in high numbers and neurofibrillary tangles in the cortex and hippocampus. Brains were promptly removed at autopsy and dissected. Tissue blocks were frozen and kept at −20°C. Slide-mounted microtome section (10 μm thick) were inubated for 45 minutes at room tempeature with 1 nM [$^3$H]SCH 23390 in 50 mM Tris HCl containing 120 mM NaCl, 5 mM KCl, mM CaCl$_2$ and MgCl$_2$, pH 7.4, washed for 5 minutes in fresh cold buffer and rapidly dried under a stream of cold air. Blanks were obtained by coincubation with 10$^{-6}$ cis-flupentixol. To generate autoradiograms the incubated tissues were exposed to [$^3$H]Ultrofilm (LKB, Sweden), together with [$^3$H]standards. Films were analyzed by microdensitometry using a computerized image-analysis sytem.

The above findings indicate that selective dopamine D1 receptors agonists are useful for the treatment of SDAT and more generally for the treatment of primary degenerative dementia, e.g. senile dementia.

The selective dopamine D1 receptor agonists for use in accordance with the invention include e.g. the compound known in the literature under the code name SKF 38393 (Setler et al.,. European J. Pharmacol. 50, 419 –430, 1978) or an indolophenanthridine of formula I

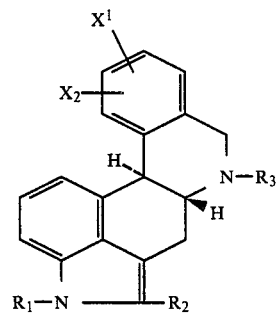

wherein
- R$_1$ and R$_3$ independently are hydrogen, (C$_{1-4}$)alkyl, (C$_{3-5}$)alkenyl wherein the double bond is not adjacentn to the nitrogen atom, (C$_{3-6}$)cycloalkyl(C$_{1-3}$)alkyl, phenyl(C$_{1-3}$)alkyl optionally substituted in the phenyl ring by (C$_{1-4}$)alkyl, (C$_{1-4}$)alkoxy, hydroxy or halogen, or 2- or 3-furyl(C$_{1-3}$)alkyl,
- R$_2$ is hydrogen, chlorine, bromine or methyl,
- X$_1$ and X$_2$ independently are hydrogen, (C$_{1-4}$)alkyl, (C$_{1-4}$)alkooxy, hydroxy, halogen or trifluoromethyl, in free base or pharmaceutically acceptable acid addition salt form.

The compounds of formula I and their pharmaceutically acceptable acid addition salts as well as a process for their production are known e.g. from U.S. Pat. No. 4,634,708. This patient also discloses the use of the compounds as dopamine receptor stimulants, e.g. both in the treatment of congestive cardiac insufficiency and of hypertension, or of renal failure with reduced urine excretion, as selective dopaminergic active agents, e.g. for the treatment of Parkinson's disease, and as analgesic agents, e.g. in the treatment of pain.

The utility according to the inventtion of selective dopamine D1 receptor agonists was confirmed in clinical trials with healthy volunteers and patients suffering from clinically diagnosed SDAT. The reactios of the patients suffering from SDAT in cognition and vigilance tests were compared with those of control groups. With the (−)-(6aR,12bR)-4,6,6a,7,8,12b-hexahydro-7-methylindolo[4,3-ab]phenanthridine, 7-methylindolo [4,3 ab ]phenanthrideine, for example, significant improvements in cognitive functions such as orientation and memory could be achieved after repeated oral administration of up to 30 mg/day during approx. 10 weeks. The compound was well tolerated by the patients and the healthy volunteers.

The selective dopamine D1 receptor agonists are therefore useful for the treatment of primary degenerative dementia, e.g. senile dementia, particularly SDAT.

The present invention accordingly provides a selective dopamine D1 receptor agonist for use in the treatment of primary degenerative dementia, e.g. senile dementia, particularly SDAT.

The present invention further provides a method of treating primary degenerative dementia, e.g. senile dementia, particularly SDAT, which comprises administering to a subject in need of osuch treatment a selective dopamine D1 receptor agonist. The invention also provides a pharmaceutical composition comprising a selective dopamine D1 receptor agonist, for use in the treatment of prmary degenerative dementia, e.g. senile dementia, particularly SDAT. Such compositions may be formulated in conventional malnner, so as to be for example a solution or a tablet.

In accordance with the present invention it has furthermore surprisingly been found that selective dopamine D1 receptor agonists are useful as antidepressants, anxiolytics and anti-obesity agents.

The selective dopamine D1 receptor agonists of formula I and their pharmaceutically acceptable acid addition salts have been found to be particularly suitable for said uses.

The utility of selective dopamine D1 receptor agonists as anti-depressants is indicated by animal tests, e.g. by the inhibition of tetrabenazine-induced catalepsy and ptosis in the rat. Groups of 6 rats of a Sprague-Dawley derivation receive the test substance 30 minutes before tetrabenazine (10 mg/kg i.p.). 40 Minutes after tetrabenazine the catalepsy of each rat is estimated by placing the forepaws on a 7 cm high wooden block. The time for which the animal remain in this unnatural position is measured, up to a maximum of 45 seconds. Immediately after determining the catalepsy, the degree of ptosis is scored on a 4-point scale. No ptosis is represented by 1 whereas a score of 4 indicates complete eye-closure. The values from the separately scored eyes are added, so that the maximum score possible is 8. If a catalepsy of 29 seconds or less is observed, the tetrabenazine-induced catalepsy is said to be antagonised. Rats with a ptosis score of less than 3 are said to be protected against the ptotic effect of tetrabenazine. This procedure is repeated 60 minutes after tetrabenazine. The antagonistic effects are expressed as percentages.

In the above test selective dopamine D1 receptor agonists inhibit the tetrabenazine-induced catalepsy and ptosis upon administering doses of 5 to 50 mg/kg i.p. For example with the (−)-(6aR,12bR)-4,6,6a,7,8,12b-hexahydro-7-methylindolo[4,3-ab]phenanthridine, a 100% inhibition of the catalepsy and a 33% inhibition of the ptosis were observed at a dose of 30 mg/kg i.p.

Selective dopamine D1 receptor agonists also show activity in the behavioral despair test [R. D. Porsolt et al., Arch. Int. Pharmacodyn., 229, 327-336 (1977)]upon administering does of 10 to 100 mg/kg p.o. With the above mentioned compound, for example, a dose of 30 mg/kg p.o. resulted in an almost 50 % reduction of immobility time in two separate experiments.

Selective dopamine D1 receptor agonists are therefore useful as antidepressants.

The present invention accordingly provides a selective dopamine D1 receptor agonist, preferably a compound of formula I in free base form or in pharmaceutically acceptable acid addition salt form, for use as an antidepressant.

The present invention further provides a method of treating depression, which comprises administering to a subject in need of such treatment a selective dopamine D1 receptor agonist, preferably a compound of formula I or a pharmaceutically acceptable acid addition salt thereof. The acid addition salt forms exhibit the same order of activity as the free bases. The invention also provides a pharmaceutical composition comprising a selective dopamine D1 receptor agonist, preferably a compound of formula I in free base form or in pharmaceutically acceptable acid addition form, for use in the treatment of depressions. Such compositions may be formulated in conventional manner, so as to be for example a solution or a tablet.

The utility of selective dopamine D1 receptor agonists as anxiolytics is indicated by animal tests, e.g. by the four plates test according to C. Aron et al., Neuropharmacology 10, 459 - 469 (1971). In this test the selective dopamine D1 receptor agonists show activity upon administering doses of 10 to 100 mg/kg p.o. The (−)-(6aR,12bR)-4,6,6a,7,8,12b-hexahydro-7-methyl-indolo[4,3-ab]phenanthridine, for example, significantly prevents the inhibition of the exploratory behaviour at a dose of 30 mg/kg p.o.

Selective dopamine D1 receptor agonists are therefore useful as anxiolytics.

The present invention accordingly provides a selective dopamine D1 receptor agonist, preferably a compound of formula I in free base form or in pharmaceutically acceptable acid addition salt form, for use as an anxiolytic.

The present invention further provides a method of treating anxiety, which comprises administering to a subject in need of such treatment a selective dopamine D1 receptor agonist, preferably a compound of formula I or a pharmaceutically acceptable acid addition salt thereof. The acid addition salt forms exhibit the same orer of activity as the free bases. The invention also provides a pharmaceutical composition comprising a selective dopamine D1 receptor agonist, preferably a compound of formula I in free base or in pharmaceutically acceptable acid addition form, for use in the treatment of anxiety. Such compositions may be formulated in conventional manner, so as to be for example a solution or a tablet.

The utility of selective dopamine D1 receptor agonists as antiobesity agents is indicated by animal tests, e.g. by their ability to decrease body weight and food consumption in the dog upon administering doses of 7 to 28 mg/kg/day, or their activity in the Competitive Feeding Situation Test.

In this test, pairs of male OF-1 mice are forced to compete over 10 minutes for a single food pellet by depriving them of food for 6 hours prior to placing both mice in a neutral cage. Because of the close proximity between the mice, the tendency to eat is competitively offset by the tendency to interact socially. One partner receives the drug and the other receives the placebo by the oral route, 1 hour before testing. Frequencies and durations of social activities and eating bouts are records for both animals. Drug effects are determined by calculating the mean differences between the behavioural responses of drugged and placebo-treated partners (within groups). In all cases 8 pairs of mice/treatment are tested, the Wilcoxon sign rank test being used to judge significances of effects within groups (p<0.05, 2-tailed). A separate group in which both partners receive the vehicle serves as an independent control. Differences between the scores of these mice and the test groups are judged using the Mann-Whitney U test (i.e. across group comparisons).

In the above test selective dopamine D1 receptor agonists induced a dose-dependent reduction of eating upon administering doses of 3 too 30 mg/kg p.o., whereas at the same dosages the number of social interactions did not change significantly. For example with the (−)-(6aR,12bR)-4,6,6a,7,8,12b-hexahydro-7-methyl-indolo[4,3-ab]phenanthridine, a dose of 10 mg/kg p.o. resulted in a decrease of 43% in frequency and of 85% in duration of the eating bouts.

Selective dopamine D1 receptor agonists are therefore useful as anti-obesity agents.

The present invention accordingly provides a selective dopamine D1 receptor agonist, preferably a compound of formula I in free base form or in pharmaceutically acceptable acid addition salt form, for use an an anti-obesity agent.

The present invention further provides a method of treating obesity, which comprises administering to a subject in need of such treatment a selective dopamine D1 receptor agonist, preferably a compound of formula I or a pharmaceutically acceptable acid addition salt thereof. The acid addition salt forms exhibit the same order of activity as the free bases. The invention also provides a pharmaceutical composition comprising a selective dopamine receptor agonist, preferably a compound of formula I in free base or in pharmaceutically acceptable acid addition form, for use in the treatment of obesity. Such compositions may be formulated in conventional manner, so as to be for example a solution or a tablet.

The various indications mentioned above suggest that selective dopamine D1 receptor agonists are also useful in schizophrenics.

The present invention accordingly provides a selective dopamine D1 receptor agonist, preferably a compound of formula I in free base for or in pharmaceutically acceptable acid addition salt form, for use in the treatment of schizophrenia.

The present invention further provides a method of treating schizophrenia, which comprises administering to a subject in need of such treatment a selective dopamine D1 receptor agonist, preferably a compound of formula I or a pharmaceutically acceptable acid addition salt thereof. The acid addition salt forms exhibit the same order of activity as the free bases. The invention also provides a pharmaceutical composition comprising a selective dopamine D1 receptor agonist, preferably a compound of formula I in free base or in pharmaceutically acceptable acid addition form, for use in the treatment of schizophrenia. Such compositions may be formulated in conventional manner, so as to be for example a solution or a tablet.

For all above mentioned indications, the appropriate dosage will of course vary depending upon, for example, the compound employed, the host, the mode of administration and the nature and severity of the condition being treated. However, in general, satisfactory results are indicated to be obtained at daily dosages from about 1 to 100 mg/kg animal body weight. In larger mammals, for example humans, an indicated daily dosage is in the range from about 20 mg to about 200 mg.

The compounds for use according to the invention may be administered by any conventional route, in particular enterally, preferably orally, e.g. in the form of tablets or capsules, or parenterally, e.g. in the form of injectable solutions or suspensions.

Suitable dosage forms, e.g. for oral administration, contain from about 5 to 100 mg of a compound for use according to the invention, together with a pharmaceutically acceptable diluent or carrier therefor.

The present invention moreover provides the use of a selective dopamine D1 receptor agonist for the manufacture of a pharmaceutical composition for treating primary degenerative dementia, depression, anxiety, obesity or schizophrenia.

The preferred selective dopamine D1 receptor agonist for use according to the invention is the (−)-(6aR,12bR)-4,6,6a,7,8,12b-hexahydro-7-methylidolo[4,3-ab]phenanthridine. The preferred indication is SDAT.

Gelatine capsules having the following composition may be prepared according to conventional methods and are suitable for use in the treatment of primary degenerative dementia, e.g. SDAT, depression, anxiety, obesity or schizophrenia:

| Compound of formula I, e.g. (-)-trans-4,6,6a,7,8,12b-hexahydro-7-methyl-indolo[4,3-ab]phenanthridine in free base form | 10 mg |
| --- | --- |
| Lactose | 165.5 mg |
| Silicium dioxide (Aerosil 200) | 1.5 mg |
| Corn Starch | 120 mg |
| Magnesium stearate | 3 mg |
| total | 300.0 mg |
| empty capsule | 77.0 mg |
| final weight | 377.0 mg |

What we claim is:

1. A method of treating primary degenerative dementia which comprises administering to a subject in need of said treatment a selective dopamine D1 receptor agonist in an amount effective for treating primary degenerative dementia.

2. A method according to claim 1 in which the primary degenerative dementia is senile dementia of the Alzheimer type.

3. A method of treating primary degenerative dementia according to claim 1 in which the selective dopamine D1 receptor agonist is a compound of formula I

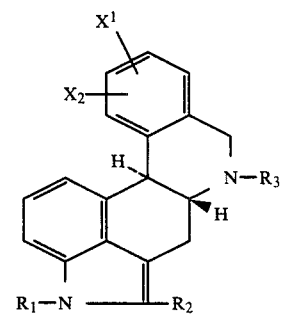

wherein
$R_1$ and $R_3$ independently are hydrogen, $(C_{1-4})$alkyl, $(C_{3-5})$alkenyl wherein the double bond is not adjacent to the nitrogen atom, $(C_{3-6})$cycloalkyl$(C_{1-3})$alkyl, phenyl$(C_{1-3})$alkyl optionally substituted in the phenyl ring by $(C_{1-4})$alkyl, $(C_{1-4})$alkoxy, hydroxy or halogen, or 2- or 3-furyl$(C_{1-3})$alkyl,
$R_2$ is hydrogen, chlorine, bromine or methyl, $X_1$ and $X_2$ independently are hydrogen, $(C_{1-4})$alkyl, $(C_{1-4})$alkoxy, hydroxy, halogen or trifluoromethyl, 4. A method according to claim 2 in nwhich the selective dopamine D1 receptor agonistt is (—)-(6aR,12bR)-4,6,6a,7,8,12b-hexahydro-7-methylindolo[4,3-ab]phenanthridine in free base or pharmaceutically acceptable acid addition salt form.

5. A method according to claim 1 in which the selective dopamine D1 receptor agonist in administered at a daily dosage of form 1 to 100 mg/kg of body weight.

6. A method according to claim 1 in which 20mg to 200 mg of the selective dopamine D1 receptor agonist is administered daily.

7. A method according to claim 1 in which 5 mg to 100 mg of the selective dopamine D1 receptor agonist is administered per unit dose.

* * * * *